(12) United States Patent
Schertzer et al.

(10) Patent No.: US 9,150,468 B2
(45) Date of Patent: Oct. 6, 2015

(54) METHOD OF PRODUCING OLEFINS VIA METATHESIS

(75) Inventors: Bryan M Schertzer, Geneva, IL (US); Karol L. Grela, Warsaw (PL); Justyna Czaban, Michalowo (PL)

(73) Assignee: Nalco Company, Naperville, IL (US)

(*) Notice: Subject to any disclaimer, the term of this patent is extended or adjusted under 35 U.S.C. 154(b) by 658 days.

(21) Appl. No.: 13/246,994

(22) Filed: Sep. 28, 2011

(65) Prior Publication Data

US 2013/0079575 A1 Mar. 28, 2013

(51) Int. Cl.
*C07C 2/08* (2006.01)
*C07C 2/06* (2006.01)
*C07C 6/04* (2006.01)

(52) U.S. Cl.
CPC .............. *C07C 6/04* (2013.01); *C07C 2531/22* (2013.01); *C07C 2531/24* (2013.01)

(58) Field of Classification Search
USPC .................................. 585/643–647; 422/231
See application file for complete search history.

(56) References Cited

U.S. PATENT DOCUMENTS

| | | | |
|---|---|---|---|
| 4,334,998 A * | 6/1982 | Rios et al. ...................... | 210/617 |
| 5,831,108 A | 11/1998 | Grubbs et al. | |
| 6,111,121 A | 8/2000 | Grubbs et al. | |
| 6,215,019 B1 | 4/2001 | Pederson et al. | |
| 6,660,813 B2 * | 12/2003 | Wagener et al. ................. | 526/71 |
| 7,507,854 B2 * | 3/2009 | Lee et al. ...................... | 560/205 |
| 2002/0022741 A1 | 2/2002 | Pederson et al. | |
| 2003/0023123 A1 | 1/2003 | Paulson et al. | |
| 2004/0097745 A9 | 5/2004 | Grubbs et al. | |
| 2006/0211905 A1* | 9/2006 | Forman et al. ................. | 585/645 |

FOREIGN PATENT DOCUMENTS

CN 1423629 A 6/2003
WO WO 01/36368 A2 5/2001

OTHER PUBLICATIONS

Dinger, et al., "High Turnover Numbers with Ruthenium-Based Metathesis Catalysts" in Adv. Synth. Catal., 2002, 344(6-7), pp. 671-677—month unknown.*
Lide, CRC Handbook of Chemistry and Physics, 91st ed., 2011 Internet Version—month unknown.*
Fair, et al., "Gas Absorption and Gas-Liquid System Design" in Perry's Chemical Engineer's Handbook, 7th edition, R. H. Green and D. W. Perry, eds., McGraw-Hill, 1997—month unknown.*
Kuhn, Kevin M., et al.; Effects of NHC-Backbone Substitution on Efficiency in Ruthenium-Based Olefin Metathesis; J. Am. Chem. Society, 2009; Published Mar. 24, 2009; Received by Publisher Jan. 5, 2009.

(Continued)

*Primary Examiner* — In Suk Bullock
*Assistant Examiner* — Youngsul Jeong
(74) *Attorney, Agent, or Firm* — Leydig, Voit & Mayer, Ltd.

(57) ABSTRACT

Disclosed is a method of producing an organic compound. The method uses a metathesis catalyst in a coupling reaction of an olefin. The method comprises the steps of introducing the olefin into a container; either placing the container under vacuum or bubbling a gas through the olefin; adding an additive with the olefin; mixing the olefin and the additive, the mixing creating a mixture; adding an amount of the metathesis catalyst to the mixture, the amount being less than about 100 ppm by weight of the mixture; and optionally heating the mixture to a temperature, the temperature being greater than room temperature.

22 Claims, 6 Drawing Sheets

(56) References Cited

OTHER PUBLICATIONS

Kuhn, Kevin M., et al.; Low Catalyst Loadings in Olefin Metathesis: Synthesis of Nitrogen Heterocycles by Ring-Closing Metathesis; Organic Letters, American Chemical Society; Published Feb. 8, 2010.

Bantreil, Xavier, et al.; Ruthenium Complexes Bearing Two N-Heterocyclic Carbene Ligands in Low Catalyst Loading Olefin Metathesis Reactions; Organometallics article, American Chemical Society; Published Jun. 4, 2010.

Abbas et al., "As low as reasonably achievable catalyst loadings in the cross metathesis of olefins with ethyl acrylate," *Tetrahedron Lett.*, 12(5), pp. 984-987, 2010.

Bielawski et al., "Highly Efficient Ring-Opening Metathesis Polymerization (ROMP) Using New Ruthenium Catalysts Containing N-Heterocyclic Carbene Ligands," *Angew. Chem. Int. Ed.*, 39(16), pp. 2903-2906, 2000.

Boeda et al., "Phosphabicyclononane-Containing Ru Complexes: Efficient Pre-Catalysts for Olefin Metathesis Reactions," *J. of Org. Chem.*, 73(1), pp. 259-263, 2008.

Buchowicz et al., "Catalytic activity and selectivity of Ru(=CHPh)Cl$_2$(PCy$_3$)$_2$ in the metathesis of linear alkenes," *J. of Mol. Catal. A: Chem.*, 148, pp. 97-103, 1999.

Chabanas et al., "Re-Based Heterogeneous Catalysts for Olefin Metathesis Prepared by Surface Organometallic Chemistry: Reactivity and Selectivity," *Chem. Eur. J.*, 9(4), pp. 971-975, 2003.

Clavier et al., "Sustainable Concepts in Olefin Metathesis," *Angew. Chem. Int. Ed.*, 46, pp. 6786-6801, 2007.

Czaban et al., "Low Catalyst Loadings in Self-Metathesis of 1-Dodecene," *Adv. Synth Catal.*, 355, pp. 1997-2006, 2013.

Dinger et al., "High Turnover Numbers with Ruthenium-Based Metahesis," *Adv. Synth. Catal.*, 344 (6+7), pp. 671-677, 2002.

Forman et al., "A Convenient System for Improving the Efficiency of First-Generation Ruthenium Olefin Metathesis Catalysts," *Organometallics*, 24(19), pp. 4528-4542, 2005.

Fürstner et al., "Comparative Investigation of Ruthenium-Based Metathesis Catalysts Bearing N-Heterocyclic Carbene (NHC) Ligands," *Chem. Eur. J.*, 7(15), pp. 3236-3253, 2001.

Fürstner, Alois, "Olefin Metathesis and Beyond," *Angew. Chem. Int. Ed.*, 39, pp. 3012-3043, 2000.

Fyles et al., "Synthesis of Lipophilic 18-Crown-6 Diacids for the Membrane Transport of Alkaline-Earth Cations," *J. of Org. Chem.*, 49(5), pp. 753-761, 1984.

Grubbs, Robert, "The Development of Functional Group Tolerant Romp Catalysts," *J. of Macromolecular Sci., Part A: Pure and Appl. Chem.*, 31(11), pp. 1829-1933, 1994.

Grubbs et al., "Recent Advances in Olefin Metathesis and Its Application in Organic Synthesis," *Tetrahedron*, 54, pp. 4413-4450, 1998.

Hong et al., "Prevention of Undesirable Isomerization during Olefin Metathesis," *J. Am. Chem. Soc.*, 127(49), pp. 17160-17161, 2005.

Jordaan et al., "Experimental and DFT investigation of the 1-octene metathesis reaction mechanism with the Grubbs 1 precatalyst," *J. of Mol. Catal. A: Chem.*, 254, pp. 145-154, 2006.

Jordaan et al., "Ruthenium Catalyst with a Chelating Pyridinyl-Alcoholato Ligand for Application in Linear Alkene Metathesis," *Adv. Synth. Catal.*, 349, pp. 184-192, 2007.

Kadyrov, Renat, "Low Catalyst Loading in Ring-Closing Metathesis Reactions," *Chem. Eur. J.*, 19, pp. 1002-1012, 2013.

Kong et al., "Synthesis of the HCV Protease Inhibitor Vaniprevir (MK-7009) Using Ring-Closing Metathesis Strategy," *J. of Org. Chem.*, 77, pp. 3820-3828, 2012.

Nosse et al., "Optimization of Ring-Closing Metathesis: Inert Gas Sparging and Microwave Irradiation," *Adv. Synth. Catal.*, 347, pp. 1869-1874, 2005.

Nicolaou et al., "Metathesis Reactions in Total Synthesis," *Angew. Chem. Int. Ed.*, 44, pp. 4490-4527, 2005.

Proverb et al., "Chemical Optimization of the ASA Sizing System," *TAPPI Papermakers Conference*, pp. 91-93, 1989.

Samojlowicz et al., "Ruthenium-Based Olefin Metathesis Catalysts Bearing N-Heterocyclic Carbene Ligands," *Chem. Rev.*, 109(8), pp. 3708-3742, 2009.

Sanford et al., "Mechanism and Activity of Ruthenium Olefin Metathesis Catalysts," *J. Am. Chem. Soc.*, 123(27), pp. 6543-6554, 2001.

Schalkwyk et al., "A Comparison of the Activity of Homogeneous Tungsten and Ruthenium Catalysts for the Metathesis of 1-Octene," *Adv. Synth Catal.*, 344 (6+7); pp. 781-788, 2002.

Schuster et al., "Olefin Metathesis in Organic Chemistry," *Angew. Chem. Int. Ed. Eng.*, 36, pp. 2036-2056, 1997.

Smith, David, "ASA components, their synthesis & relative sizing performances," *Conference on Scientific and Technical Advances in the Internal & Surface Sizing of Paper & Board*, 15 pp., Dec. 3, 1999.

Thayer, Ann M., "Making Metathesis Work," *Chem. & Eng. News*, pp. 37-47, Feb. 12, 2007.

Trnka et al., "The Development of L$_2$X$_2$Ru=CHR Olefin Metathesis Catalysts: An Organometallic Success Story," *Acc. Chem. Res.*, 34(1), pp. 18-29, 2001.

Vosloo et al., "The metathesis of 1-octene with the W(O-2,6-C$_6$H$_3$X$_2$)$_2$CL$_4$/R$_4$Sn catalysis system," *J. of Mol. Catal. A: Chem.*, 115, pp. 119-205, 1997.

Williams et al., "Highly Selective Metathesis of 1-Octene in Ionic Liquids," *Organometallics*, 25(12), pp. 3088-3090, 2006.

European Patent Office, Supplementary European Search Report in European Patent Application No. 12834855.4, May 6, 2015, 9 pages.

* cited by examiner

Formula 1

Group A

Group B

Cl  2 Cl  4 F

METHOD OF PRODUCING OLEFINS VIA METATHESIS

FIELD OF THE INVENTION

The invention relates generally to the production of organic compounds via catalytic olefin metathesis reaction, and more particularly relates to methods of more efficiently carrying out the catalytic olefin metathesis reaction.

BACKGROUND

Olefin metathesis is an emerging commercial technology that may allow access to new classes of organic compounds, several of which could be used as raw materials to more efficiently and cost-effectively produce useful organic products.

A particular area of research related to metathesis reactions has been performed by a group of researchers at the California Institute of Technology. Two publications, authored by Kevin M. Kuhn et al., describe some of the research related to metathesis reactions using ruthenium-based catalysts. A publication by Xavier Bantreil et al. discloses the synthesis of several ruthenium indenylidene complexes that may be used in olefin metathesis reactions.

Further research in the art has related to the additives that may be added to metathesis reactions to inhibit isomerization. For example, U.S. Pat. No. 7,507,854, to Lee et al., discloses an invention related to the use of isomerization inhibitors in olefin metathesis reactions. The inhibitors are low molecular weight organic acids such as formic acid, acetic acid, benzoic acid, and the like.

Accordingly, there is a need for an efficient, cost-effective method of performing olefin metathesis reactions. Desirably, the method would provide high yield of desired product with minimal isomerization. More desirably, the method would minimize metathesis catalyst load, thereby significantly reducing cost.

SUMMARY OF THE INVENTION

The present disclosure provides for a method of producing an organic compound. The method uses a metathesis catalyst in a coupling reaction of an olefin. The method comprises introducing the olefin into a container; adding an additive to the container; mixing the olefin and the additive, the mixing creating a mixture; placing the container under vacuum; adding an amount of the metathesis catalyst to the mixture thereby creating a second mixture, the amount being less than about 100 ppm by weight of the second mixture; and optionally heating the second mixture to a temperature, the temperature being greater than room temperature.

Additionally, the present disclosure provides for a method of producing an organic compound. The method uses a metathesis catalyst in a coupling reaction of an olefin. The method comprises introducing the olefin into a container; bubbling a gas through the olefin; adding an additive to the container, the adding creating a mixture; adding an amount of the metathesis catalyst to the mixture thereby creating a second mixture, the amount being less than about 100 ppm by weight of the second mixture; and optionally heating the second mixture to a temperature, the temperature being greater than room temperature.

The present disclosure further provides for a method of producing an organic compound. The method uses a metathesis catalyst in a coupling reaction of an olefin. The method comprises introducing the olefin into a container; adding an additive to the container, the adding creating a mixture; adding an amount of the metathesis catalyst to the mixture thereby creating a second mixture, the amount being less than about 100 ppm by weight of the second mixture; and optionally heating the second mixture to a temperature, the temperature being greater than room temperature; wherein an inert gas is bubbled through at least one of the mixture and the second mixture.

These and other features and advantages of the present invention will be apparent from the following detailed description, in conjunction with the appended claims.

BRIEF DESCRIPTION OF THE DRAWINGS

The benefits and advantages of the present invention will become more readily apparent to those of ordinary skill in the relevant art after reviewing the following detailed description and accompanying drawings, wherein.

DETAILED DESCRIPTION OF THE INVENTION

Definitions

For purposes of this patent application, the following terms have the definitions set forth below:

"About" means within one integer of the value that follows.

"Additive" means a chemical that itself is not necessary in the reaction, but may modify the reaction to achieve greater conversion, yield, or selectivity of a metathesis reaction. Benzoquinone is a family of additives that may be used in metathesis reactions.

Figure 1:
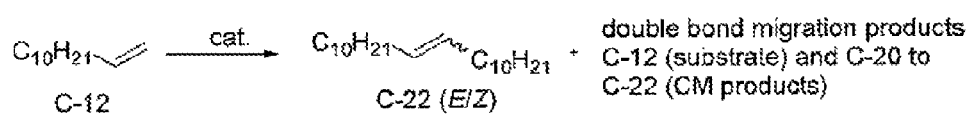
FIG. 1 is the chemical formula that represents Formula 1.

"Coupling reaction" means a reaction that, using two olefins, creates an organic compound having a double bond that is interior to the carbon chain. The two olefins may have the same chemical formula, and when they do, the reaction is a homo-dimerization reaction. Formula 1, shown in FIG. 1, illustrates one particular homo-dimerization reaction, and ethylene gas is additionally given off in the reaction (not shown).

"Mixing" means agitating a substance by any means possible.

"Mixture" means a substance that is made up of more than one chemical compound.

"Vacuum" means any pressure that is below ambient pressure.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiment illustrated.

It should be further understood that the title of this section of this specification, namely, "Detailed Description of the Invention," relates to a requirement of the United States Patent Office, and does not imply, nor should be inferred to limit the subject matter disclosed herein.

In an embodiment, the method may comprise introducing a second olefin into the container.

In an embodiment, the olefin can be n-dodecene.

In an embodiment, the coupling reaction can be a homo-dimerization reaction.

Figure 2:
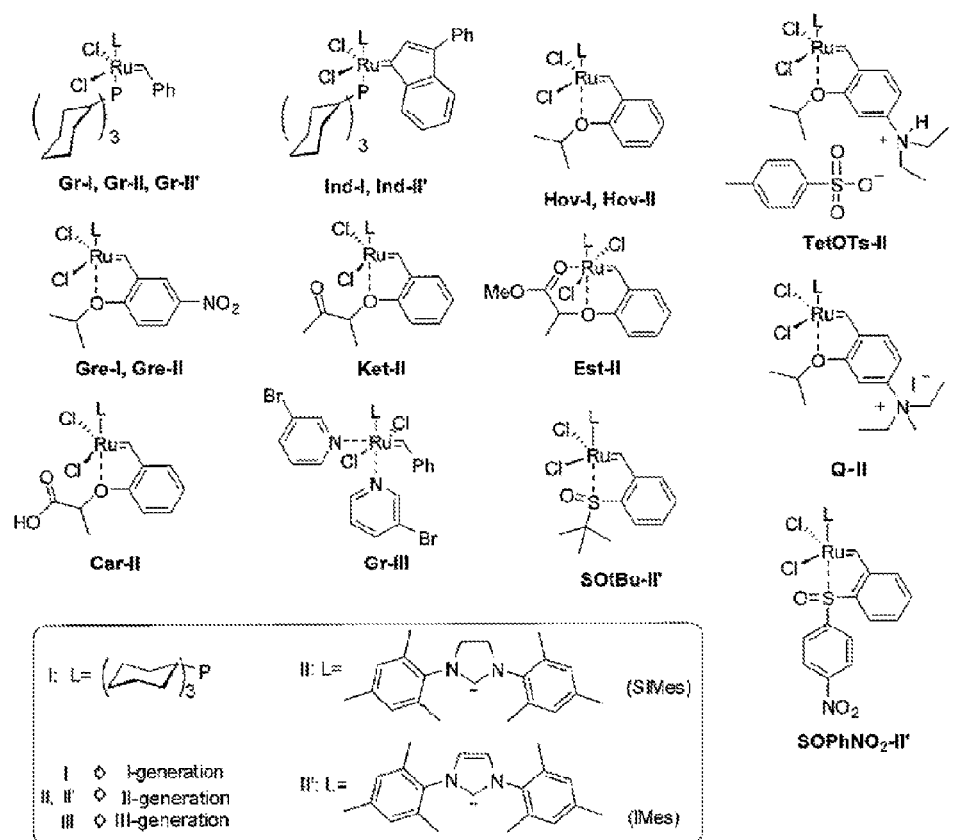
FIG. 2 is an illustration of the chemical structures that make up Group A.

In an embodiment, the metathesis catalyst is selected from the group consisting of the chemicals listed in Group A (illustrated in FIG. 2), Group B (illustrated in FIG. 5), and combinations thereof.

In an embodiment, the reaction is performed under vacuum. For this embodiment, the vacuum may be less than about 50 mbar. The vacuum can be about 40 mbar. A preferred embodiment the vacuum is less than about 1 mbar; however, such a vacuum may be difficult to economically achieve in a production setting.

In an embodiment, the amount of the metathesis catalyst added to the mixture is less than about 40 ppm by weight of the mixture.

In an embodiment, the amount of the metathesis catalyst added to the mixture is about 10 ppm by weight of the mixture.

The organic compound produced by the method may have the chemical formula $C_nH_{2n}$ or RHC=CHR. One particular embodiment of the invention produces an organic compound with the chemical formula $C_{22}H_{44}$.

In an embodiment, a gas is bubbled through the reactants. In such an embodiment, the gas may be an inert gas. In a preferred embodiment, the gas is argon.

In an embodiment, the metathesis catalyst added in portions.

In an embodiment, the metathesis catalyst is dissolved in a solvent.

If the method employs heating, a preferred embodiment calls for the mixture to be heated to about 60° C.

An additional embodiment of the invention is a method of improving yield in a chemical reaction, the chemical reaction producing an organic chemical with the formula $C_nH_{2n}$. The method comprises the steps of adding an amount of a metathesis catalyst to a solution, the solution comprising an olefin, the adding conducted under vacuum, the adding creating a mixture, the amount of the metathesis catalyst being less than 100 ppm by weight of the mixture; mixing the metathesis catalyst and the olefin under vacuum; and optionally heating the mixture.

Yet another embodiment is a method for carrying out a metathesis reaction, the method comprising a vessel, the vessel comprising contents. The method comprises the steps of placing the contents under vacuum; adding an amount of a metathesis catalyst to the contents, the contents comprising an olefin, the amount of the metathesis catalyst being less than about 100 ppm by weight of the contents; and optionally heating the contents to a temperature greater than room temperature.

EXAMPLES

Several metathesis catalysts were tested in Warsaw, Poland, in coupling reactions of olefins, with the goal of producing the highest conversion of coupling reaction product using the least amount of catalyst load. The Group A catalysts were tested. Preliminary experiments were made at relatively high catalyst loads to check susceptibility of starting olefin for isomerization. The preliminary experiments employed 1 mole percent of the Hov-II catalyst at 60° C. The olefin concentration was 0.2 molar in toluene, with the reaction conducted under Argon. After 4 hr, the maximum conversion was 7%.

Figure 3:
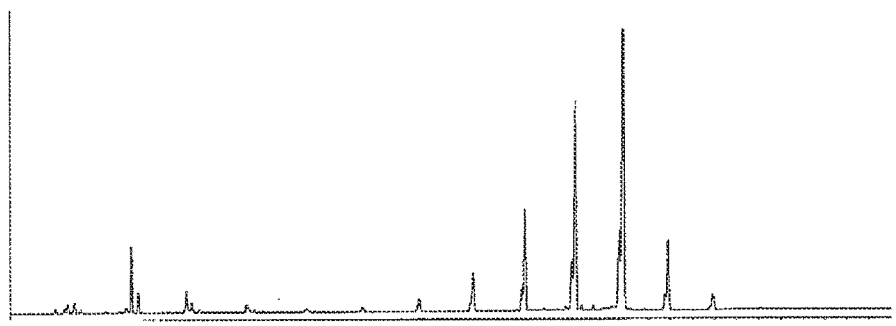
FIG. 3 is a chromatography profile of the product produced in the preliminary experiments described in the Examples.

The same reaction was then conducted without solvent (in neat olefin). The catalyst was added as a concentrated solution in a minimal amount of solvent (toluene or dichloromethane). After some experimentation, it was discovered that lowered pressure was beneficial for the reaction, leading to much higher conversions. The reaction was conducted at 40 mbar absolute pressure using a membrane pump. Though an increase in the conversion to the coupled product was observed, an increase in unwanted by-products was also achieved (as shown in FIG. 3 in the gas chromatography profile taken of a sample after 2 hr of this reaction).

These results provided the basis for further experimentation in order to optimize conversion and selectivity, with the goal to decrease catalyst loading below 10 ppm, if possible.

Example 1

Figure 4:
FIG. 4 is a chromatography profile of the product produced in Example 1.

Two metathesis reactions employing Gr-II catalysts were executed with and without 2-chloro-1,4-benzoquinone ("the additive") under otherwise identical conditions. The reactions were carried out using 500 ppm Gr-II catalyst at 40 mbar pressure and room temperature for 6 hr. While without the additive, a significant amount of isomerization was observed, the reaction in the presence of 1000 ppm of the additive was much cleaner, leading mostly to the desired product (E/Z ratio 85:15). Shown in FIG. 4 is a gas chromatography profile of a sample taken after 2 hr of one of the reactions that employed the additive.

Interestingly, some I-generation catalysts lead to clean reactions even without 1,4-benzoquinone, but usually at lower conversion rates than their II-generation counterparts when conducted under similar conditions (time, temperature). In some initial experiments, the addition of 1,4-benzoquinone may have had a positive effect on the overall conversion rate.

Example 2

Optimization was conducted for two representative, commercially available catalysts: Gr-I and Ind-I, with experiments conducted at the conditions illustrated in Tables I and II respectively.

TABLE 1

Optimization for Gr-I.

| | | GC Yield (%) | |
| --- | --- | --- | --- |
| Catalyst loading (ppm) | P (mbar) | reaction without 2-chloro-1,4-benzoquinone | reaction with 2-chloro-1,4-benzoquinone |
| 500 | 40 | 90 | nd |
| 200 | 40 | 67 | nd |
| 100 | 40 | 60 | nd |
| 100 | $6 \times 10^{-2}$ | nd | 85 |
| 50 | $6 \times 10^{-2}$ | 64 | nd |
| 10 | $6 \times 10^{-2}$ | 19 | 44 |

Conditions: scale = 11 mL of dodecene; 0.1M of catalyst in toluene; 0.2M of 2-chloro-1,4-benzoquinone in toluene; room temperature; 6 hrs. Two equivalents of 2-chloro-1,4-benzoquinone relative to the catalyst were used.
nd = not determined

TABLE 2

Optimization for Ind-I.

| Catalyst loading (ppm) | P (mbar) | GC Yield (%) | |
|---|---|---|---|
| | | reaction without 2-chloro-1,4-benzoquinone | reaction with 2-chloro-1,4-benzoquinone |
| 1000 | 40 | 90 | nd |
| 500 | 40 | 88 | nd |
| 500 | $6 \times 10^{-2}$ | 89 | nd |
| 10 | $6 \times 10^{-2}$ | nd | 27 |

Conditions: scale = 11 mL of dodecene; 0.1M of catalyst in DCM; 0.2M of 2-chloro-1,4-benzoquinone in DCM; room temperature; 6 hrs. Two equivalents of 2-chloro-1,4-benzoquinone relative to the catalyst were used.
nd = not determined Eleven milliliters of olefin was placed in a reactor equipped with a septum, gas outlet, and magnetic stir bar. To the gas outlet valve, a rotary-vane pump was connected and reduced pressure was applied. After 20 min. of degassing, 20 ppm of 2-chloro-1,4-benzoquinone as 0.2 molar stock solution in dichloromethane or toluene (refer to table notes) was added. Next, 10 ppm of catalyst as 0.1 molar stock solution in dichloromethane or toluene (refer to table notes) was added. The reactions were conducted under reduced pressure (0.06 mbar) at room temperature or 60° C. (refer to table notes) for 6 hr. The progress of the reaction was monitored on-line using gas chromatography (HP5 column, FID detector), and the gas chromatography response was uncalibrated.

While performing these experiments, it was observed that decreasing the pressure and adding 2-chloro-1,4-benzoquinone allowed for reaction product having higher conversion and purity. Reducing the pressure below 1 mbar seemed to have some influence of the conversion. A noteworthy result for these experiments was that up to 44% conversion of raw material was possible for as low as 10 ppm catalyst load.

Example 3

Using the optimized conditions of Example 2, a small library of selected I-generation and II-generation catalysts were tested in order to learn more about the catalyst structure-reactivity relationships. For this set of experiments, two equivalents of 2-chloro-1,4-benzoquinone relative to each catalyst was used. For all products, the E/Z ratio was similar: 85:15. The results are shown in Table III below. In addition to the high conversion rates, the presence of 2-chloro-1,4-benzoquinone inhibited unwanted isomerization, leading to product in the form of a waxy, low-melting point solid. From the panel tested, the Gr-II, Gre-II, and Carb-II catalysts gave the best results and were selected for additional experimentation.

TABLE 3

Catalyst screening at 10 ppm loading.

| Catalyst | GC Yield (%) | |
|---|---|---|
| | Room Temp | 60° C. |
| Q-II | 39 | 62 |
| Carb-II | 48 | 80 |
| Ket-II | 45 | 59 |
| Est-II | 42 | 50 |
| Ind-I | 44* | 17* |
| Gr-II | 52 | 87 |
| Hov-II | 35 | 67 |
| SOtBu-II' | 12* | 31* |
| Gr-II' | 3 | 46 |
| Ind-II' | 10 | 25 |
| Gr-III | 17 | 41 |
| Gre-I | 6 | 14 |
| Gr-I | 27 | 20 |
| Hov-I | 15 | 10 |
| SOPhNO2-II' | 25* | 42* |
| Gre-II | 60 | 80 |
| TetOTs-II | 10 | 37 |

Conditions: scale = 11 mL of dodecene; 10 ppm of catalyst as 0.1 molar solution in DCM (*toluene); 20 ppm of 2-chloro-1,4-benzoquinone as 0.1 molar solution in DCM (*toluene); p = 0.06 mbar; 6 hr Example 4

It is known in the art that, for "difficult" cases of metathesis reactions, the portion-wise addition of catalysts during the reaction course leads to usually better results. A portion-wise addition regimen was tested for this set of experiments. Reactions were performed at the several catalyst loadings and conditions shown in Table IV. Catalysts were added in six portions, each portion added every one hour. 2-chloro-1,4-benzoquinone was added in one portion before adding the catalyst. As shown, even as low amounts of catalyst as 2.4 ppm of Gr-II or 4.8 ppm of Carb-II led to significant conversion of approximately 60%.

TABLE 4

Portion-wise addition of catalyst.

| Catalyst loading (ppm) | GC Yield (%) | |
|---|---|---|
| | Gr-II | Carb-II |
| 6.0 | 82 | nd |
| 4.8 | nd | 64 |
| 3.0 | nd | 43 |
| 2.4 | 60 | nd |
| 1.0 | 17 | 14 |

Conditions: scale = 11 mL of dodecene; catalysts added as 0.1 molar solution in DCM; 2-chloro-1,4-benzoquinone added as 0.1 molar solution in DCM; p = 0.06 mbar; 6 hr; 60° C.;
nd = not determined Example 5

Figure 5:
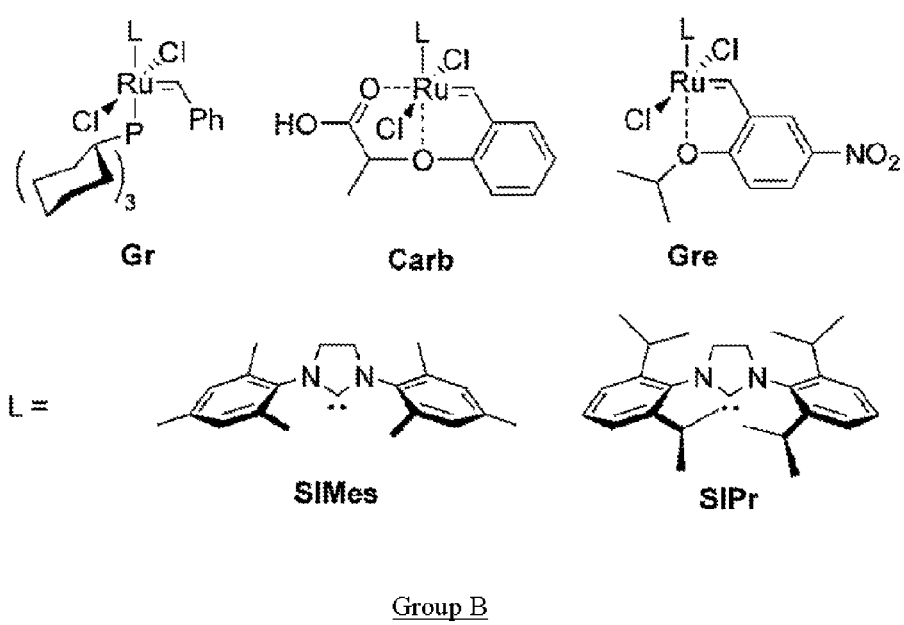
FIG. 5 is an illustration of the chemical structures that make up Group B.

Going forward, the Group B catalysts as illustrated in FIG. 5 were tested.

Figure 6:
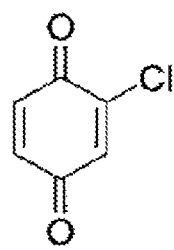
FIG. 6 is an illustration of the chemical structures that make up the benzoquinones that were tested in whole or in part in Examples 5-8.
Figure 6:
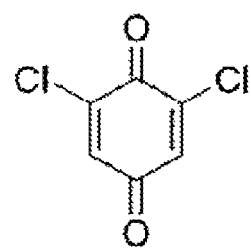
Figure 6:
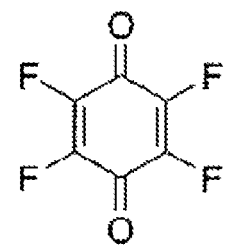

Instead of using high vacuum (≤1 mbar) as in the previous examples, a more industrial-friendly vacuum of 40 mbar was employed. Also, three benzoquinones were tested instead of the single benzoquinone tested in the previous examples. The three benzoquinones were the following: 2-chloro-1,4-benzoquinone; 2,6-dichloro-1,4-benzoquinone; and 2,3,5,6-tetrafluoro-benzoquinone, encoded as Cl, 2Cl, and 4F, with each chemical structure illustrated in FIG. 6.

The influence of the ratio of benzoquinone to ruthenium catalyst on conversion was studied with standard Grubbs-II generation SIMes catalyst ("Gr-SIMes") under fixed conditions (6 hr, p=40 mbar, scale=11 mL of dodecene). Ruthenium catalyst was added as 0.1 molar solution in DCM. Catalyst loading was either 10 ppm or 20 ppm. The respective benzoquinone, 2 or 6 equivalents relative to ruthenium, was added to the reaction as 0.1 molar solution in DCM. The progress of the reaction was monitored on-line using gas chromatography (HP5 column, FID detector), and the gas chromatography response was uncalibrated. The results of these tests are shown in Table 5 below.

TABLE 5

Influence of benzoquinone nature and ratio on conversion, yield, and selectivity.

| Benzoquinone type | Gr-SIMes equivalents | Ru 10 ppm Conversion | Yield | Selectivity | Ru 20 ppm Conversion | Yield | Selectivity |
|---|---|---|---|---|---|---|---|
| Cl | 2 | 55% | 54% | 98% | 62% | 61% | 98% |
|  | 6 | 63% | 62% | 98% | 62% | 61% | 98% |
| 2Cl | 2 | 44% | 43% | 98% | 59% | 57% | 98% |
|  | 6 | 51% | 50% | 98% | 60% | 59% | 97% |
| 4F | 2 | 30% | 29% | 97% | 53% | 50% | 92% |
|  | 6 | 35% | 33% | 97% | 58% | 57% | 97% |

Conditions: scale = 11 mL of dodecene; GrII-SIMes catalysts as 0.1M solution in DCM; benzoquinones as 0.1M solution in DCM; p = 40 mbar; 6 hr Of the 10-ppm experiments, the best yields were obtained using Cl. For higher catalyst loading, the influence of benzoquinone type was less visible. While better results were typically achieved with six equivalents of benzoquinone, the improvement in yield was not substantial. However, use of larger amounts of benzoquinone led to significant coloration of the product. Because of the increased coloration, further experiments employed the use of two equivalents of benzoquinone.

Example 6

For Example 6, the Group B catalysts were tested. The conditions and results of these experiments are shown in Tables 6-8 below.

TABLE 6

Yield and isomerization data for the Example 6 10-ppm experiments.

| Catalyst and Benzoquinone |  | Ru 10 ppm Conversion, % | Yield, % | Selectivity, % |
|---|---|---|---|---|
| Gr SIMes | none | 64 | 53 | 83 |
|  | Cl | 55 | 54 | 98 |
|  | 2Cl | 67 | 65 | 97 |
|  | 4F | 33 | 32 | 96 |
| Gr SIPr | none | 62 | 59 | 95 |
|  | Cl | 64 | 64 | 100 |
|  | 2Cl | 60 | 58 | 98 |
|  | 4F | 51 | 50 | 97 |
| Carb SIMes | none | 18 | 16 | 95 |
|  | Cl | 13 | 13 | 100 |
|  | 2Cl | 12 | 12 | 100 |
|  | 4F | 13 | 13 | 100 |
| Carb SIPr | none | 53 | 52 | 98 |
|  | Cl | 55 | 52 | 98 |
|  | 2Cl | 56 | 55 | 98 |
|  | 4F | 57 | 56 | 98 |
| Gre SIMes | none | 3 | 3 | 100 |
|  | Cl | 12 | 12 | 100 |
|  | 2Cl | 4 | 4 | 100 |
|  | 4F | 10 | 10 | 100 |
| Gre SIPr | none | 2 | 2 | 100 |
|  | Cl | 7 | 6 | 88 |
|  | 2Cl | 23 | 21 | 94 |
|  | 4F | 4 | 4 | 100 |

Conditions: scale = 11 mL of dodecene; catalysts as 0.1M solution in DCM; benzoquinones as 0.1M solution in DCM; p = 40 mbar; 6 hr

TABLE 7

Yield and isomerization data for the Example 6 20-ppm experiments.

| Catalyst and Benzoquinone |  | Ru 20 ppm Conversion, % | Yield, % | Selectivity, % |
|---|---|---|---|---|
| Gr SIMes | none | 62 | 57 | 92 |
|  | Cl | 62 | 61 | 97 |
|  | 2Cl | 61 | 59 | 97 |
|  | 4F | 56 | 50 | 92 |
| Gr SIPr | none | 91 | 75 | 82 |
|  | Cl | 49 | 48 | 97 |
|  | 2Cl | 57 | 56 | 98 |
|  | 4F | 60 | 56 | 93 |
| Carb SIMes | none | 40 | 37 | 94 |
|  | Cl | 32 | 31 | 97 |
|  | 2Cl | 58 | 52 | 90 |
|  | 4F | 34 | 33 | 96 |
| Carb SIPr | none | 62 | 60 | 97 |
|  | Cl | 75 | 73 | 96 |
|  | 2Cl | 66 | 64 | 97 |
|  | 4F | 59 | 58 | 98 |
| Gre SIMes | none | 68 | 47 | 68 |
|  | Cl | 29 | 28 | 97 |
|  | 2Cl | 34 | 33 | 96 |
|  | 4F | 13 | 13 | 100 |
| Gre SIPr | none | 67 | 60 | 90 |
|  | Cl | 42 | 40 | 95 |
|  | 2Cl | 53 | 51 | 96 |
|  | 4F | 68 | 66 | 97 |

Conditions: scale = 11 mL of dodecene; catalysts as 0.1M solution in DCM; benzoquinones as 0.1M solution in DCM; p = 40 mbar; 6 hr

TABLE 8

Yield and isomerization data for the Example 6 30-ppm experiments.

| Catalyst and Benzoquinone |  | Ru 30 ppm Conversion, % | Yield, % | Selectivity, % |
|---|---|---|---|---|
| Gr SIMes | none | 71 | 64 | 90 |
|  | Cl | 59 | 58 | 98 |
|  | 2Cl | 70 | 57 | 96 |
|  | 4F | 45 | 44 | 96 |
| Gr SIPr | none | 86 | 73 | 85 |
|  | Cl | 71 | 69 | 97 |
|  | 2Cl | 74 | 71 | 96 |
|  | 4F | 75 | 72 | 96 |
| Carb SIMes | none | 58 | 56 | 96 |
|  | Cl | 48 | 45 | 95 |
|  | 2Cl | 67 | 60 | 90 |
|  | 4F | 51 | 48 | 96 |

TABLE 8-continued

Yield and isomerization data for
the Example 6 30-ppm experiments.

Ru 30 ppm

| Catalyst and Benzoquinone | | Conversion, % | Yield, % | Selectivity, % |
|---|---|---|---|---|
| Carb SIPr | none | 70 | 68 | 97 |
|  | Cl | 71 | 69 | 97 |
|  | 2Cl | 63 | 60 | 95 |
|  | 4F | 64 | 63 | 98 |
| Gre SIMes | none | 29 | 22 | 75 |
|  | Cl | 36 | 35 | 95 |
|  | 2Cl | 38 | 37 | 96 |
|  | 4F | 22 | 20 | 94 |
| Gre SIPr | none | 83 | 68 | 83 |
|  | Cl | 61 | 58 | 96 |
|  | 2Cl | 72 | 70 | 97 |
|  | 4F | 14 | 13 | 90 |

Conditions: scale = 11 mL of dodecene; catalysts as 0.1M solution in DCM; benzoquinones as 0.1M solution in DCM; p = 40 mbar; 6 hr These experiments show that the SIPr-based catalysts typically performed better at these conditions (higher yields and less isomerization). Especially, Gr-SIPr and Carb-SIPr showed a good combination of activity and selectivity. Though very active at high vacuum, the Gre catalyst showed less efficiency at 40 mbar.

Example 7

To prove the disadvantageous effect of increasing pressure (reducing vacuum) on the reaction, the following experiments were performed, with the conditions and results shown in Tables 9-10 below.

TABLE 9

Experiments of Example 7 at 40 mbar pressure.

40 mbar

| Catalyst and Benzoquinone | | Conversion, % | Yield, % | Selectivity, % |
|---|---|---|---|---|
| Gr SIMes | none | 64 | 53 | 83 |
|  | Cl | 55 | 54 | 98 |
|  | 2Cl | 67 | 65 | 97 |
|  | 4F | 33 | 32 | 96 |
| Gr SIPr | none | 62 | 59 | 95 |
|  | Cl | 64 | 64 | 100 |
|  | 2Cl | 60 | 58 | 98 |
|  | 4F | 51 | 50 | 97 |
| Carb SIMes | none | 18 | 16 | 95 |
|  | Cl | 13 | 13 | 100 |
|  | 2Cl | 12 | 12 | 100 |
|  | 4F | 13 | 13 | 100 |
| Carb SIPr | none | 53 | 52 | 98 |
|  | Cl | 55 | 52 | 98 |
|  | 2Cl | 56 | 55 | 98 |
|  | 4F | 57 | 56 | 98 |

Conditions: scale = 11 mL of dodecene; 10 ppm of catalysts as 0.1M solution in DCM; 20 ppm of benzoquinones as 0.1M solution in DCM; 6 hr

TABLE 10

Experiments of Example 7 at 0.1 mbar pressure.

0.1 mbar

| Catalyst and Benzoquinone | | Conversion, % | Yield, % | Selectivity, % |
|---|---|---|---|---|
| Gr SIMes | none | 76 | 66 | 87 |
|  | Cl | 68 | 66 | 97 |
|  | 2Cl | 73 | 70 | 96 |
|  | 4F | 63 | 58 | 93 |

TABLE 10-continued

Experiments of Example 7 at 0.1 mbar pressure.

0.1 mbar

| Catalyst and Benzoquinone | | Conversion, % | Yield, % | Selectivity, % |
|---|---|---|---|---|
| Gr SIPr | none | 77 | 72 | 94 |
|  | Cl | 79 | 75 | 95 |
|  | 2Cl | 74 | 72 | 96 |
|  | 4F | 69 | 69 | 100 |
| Carb SIMes | none | 37 | 30 | 85 |
|  | Cl | 47 | 42 | 89 |
|  | 2Cl | 31 | 31 | 100 |
|  | 4F | 50 | 48 | 95 |
| Carb SIPr | none | 66 | 64 | 96 |
|  | Cl | 71 | 70 | 98 |
|  | 2Cl | 79 | 75 | 95 |
|  | 4F | 69 | 67 | 97 |

Conditions: scale = 11 mL of dodecene; 10 ppm of catalysts as 0.1M solution in DCM; 20 ppm of benzoquinones as 0.1M solution in DCM; 6 hr Example 8

Another method of removing ethylene from the reaction is to purge the reaction with an inert gas. The reaction was conducted in a gas washing vessel equipped with a sintered plug. Instead of performing the reaction under vacuum, argon was constantly bubbled through the reaction via the sintered plug. The gas washing vessel was carefully washed and dried prior to use. The 1-dodecene (22 mL) was degassed before use and placed in the gas washing vessel. The catalyst Carb SIMes (20 ppm, 1.4 mL) and Cl-benzoquinone (40 ppm, 0.6 mL) were added as 0.1 molar solutions in DCM. The reaction was conducted at 60° C. for 6 hr with constant bubbling of argon. After the six hours, the reaction conversion was checked by uncalibrated gas chromatography. The composition of the reaction mixture was as follows: conversion 91%; total isomers 3%; substrate isomers 6%; yield 93%.

All patents referred to herein, are hereby incorporated herein by reference, whether or not specifically done so within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the illustrated specific embodiments or examples is intended or should be inferred. The disclosure is intended to cover by the appended claims all such modifications as fall within the scope of the claims.

We claim:

1. A method of producing an organic compound having the formula $C_nH_{2n}$ using a metathesis catalyst in a coupling reaction of at least one olefin, the method comprising:
   introducing at least one olefin, a benzoquinone, and a metathesis catalyst, and optionally an organic solvent into a container thereby forming a mixture thereof, wherein the amount of the metathesis catalyst introduced into the container ranges from 2.4 ppm to about 100 ppm by weight of the mixture; and
   causing the at least one olefin in the mixture to undergo a coupling reaction while bubbling a gas through the mixture, wherein a product having the formula $C_nH_{2n}$ is provided.

2. The method of claim 1, wherein the least one olefin comprises at least two olefins.

3. The method of claim 1, wherein the gas is an inert gas.

4. The method of claim 1, wherein the gas is argon.

5. The method of claim 1, wherein the bubbling is constant during the course of the coupling reaction.

6. The method of claim 5, wherein the bubbling is performed via a sintered plug.

7. The method of claim 1, wherein the amount of the metathesis catalyst in the mixture ranges from 2.4 ppm to about 40 ppm by weight of the mixture.

8. The method of claim 7, wherein the amount of the metathesis catalyst in the mixture ranges from 2.4 ppm to about 20 ppm by weight of the mixture.

9. The method of claim 1, wherein the metathesis catalyst is selected from the group consisting of: Gr-I, Ind-I, Hov-I, Gre-I, and combinations thereof.

10. The method of claim 1, wherein the metathesis catalyst is selected from the group consisting of: Gr-II, Gr-II', Gre-II, Carb-II, Ind-II', Ket-II, Hov-II, Est-II, SOtBu-II', TetOTs-II, Q-II, SOPhNO$_2$-II', and combinations thereof.

11. The method of claim 10, wherein the metathesis catalyst is selected from the group consisting of: Gr-II, Gre-II, Carb-II, and combinations thereof.

12. The method of claim 1, further comprising heating the mixture during the coupling reaction to a temperature greater than room temperature.

13. A method of producing an organic compound having the chemical formula $C_nH_{2n}$ using a metathesis catalyst in a coupling reaction of at least one olefin, the method comprising:
introducing at least one olefin, a benzoquinone, a metathesis catalyst, and optionally an organic solvent into a container thereby forming a mixture thereof, wherein the amount of the metathesis catalyst introduced into the container ranges from 2.4 ppm to about 100 ppm by weight of the mixture; and causing the at least one olefin in the mixture to undergo a coupling reaction while bubbling a gas through the mixture, wherein a product having the formula CnH2n is provided;
wherein the conversion factor of the at least one olefin ranges from about 50 to about 90% and the coupling reaction has a selectivity factor of at least 90%.

14. The method of claim 13, wherein the at least one olefin comprises at least two olefins.

15. The method of claim 13, wherein the gas is an inert gas.

16. The method of claim 15, wherein the gas is argon.

17. The method of claim 13, wherein the amount of the metathesis catalyst in the mixture ranges from 2.4 ppm to about 40 ppm by weight of the mixture.

18. The method of claim 17, wherein the amount of the metathesis catalyst in the mixture ranges from 2.4 ppm to about 20 ppm by weight of the mixture.

19. The method of claim 13, wherein the metathesis catalyst is selected from the group consisting of: Gr-I, Ind-I, Hov-I, Gre-I, and combinations thereof.

20. The method of claim 13, wherein the metathesis catalyst is selected from the group consisting of: Gr-II, Gr-III, Gre-II, Carb-II, Ind-II', Ket-II, Hov-II, Est-II, SOtBu-II', TetOTs-II, Q-II, SOPhNO$_2$-II', and combinations thereof.

21. The method of claim 20, wherein the metathesis catalyst is selected from the group consisting of: Gr-II, Gre-II, Carb-II, and combinations thereof.

22. The method of claim 13, further comprising heating the mixture during the coupling reaction to a temperature greater than room temperature.

* * * * *